United States Patent
Morman

[19]

[11] Patent Number: 5,993,589
[45] Date of Patent: Nov. 30, 1999

[54] BREATHABLE LAMINATE INCLUDING FILLED FILM AND CONTINUOUS FILM AND METHOD FOR MAKING THE SAME

[76] Inventor: Michael T. Morman, 555 Kings Peak, Alpharetta, Ga. 30202

[21] Appl. No.: 09/256,602

[22] Filed: Feb. 23, 1999

Related U.S. Application Data

[62] Division of application No. 08/774,477, Dec. 30, 1996, Pat. No. 5,914,184.

[51] Int. Cl.$^6$ .................................................. B32B 31/00
[52] U.S. Cl. ........................ 156/229; 264/241; 264/291; 264/45.1; 264/257
[58] Field of Search ................................ 264/45.1, 241, 264/257, 291; 156/229

[56] References Cited

U.S. PATENT DOCUMENTS

| | | | |
|---|---|---|---|
| 3,438,844 | 4/1969 | Kumin | 161/150 |
| 3,679,538 | 7/1972 | Druin et al. | 161/159 |
| 3,949,128 | 4/1976 | Ostermeier | 428/152 |
| 4,013,816 | 3/1977 | Sabee et al. | 428/288 |
| 4,041,203 | 8/1977 | Brock et al. | 428/157 |
| 4,147,327 | 4/1979 | Moran | 251/174 |
| 4,187,210 | 2/1980 | Howard, Jr. | 260/42.14 |
| 4,197,150 | 4/1980 | Breidt, Jr. et al. | 156/229 |
| 4,209,563 | 6/1980 | Sisson | 428/288 |
| 4,303,708 | 12/1981 | Gebhardt et al. | 428/35 |
| 4,323,534 | 4/1982 | Desmarais | 264/176 R |
| 4,333,979 | 6/1982 | Sciaraffa et al. | 428/179 |
| 4,340,563 | 7/1982 | Appel et al. | 264/518 |
| 4,384,024 | 5/1983 | Mitchell et al. | 428/349 |
| 4,418,123 | 11/1983 | Bunnelle et al. | 428/517 |
| 4,443,511 | 4/1984 | Worden et al. | 428/198 |
| 4,443,513 | 4/1984 | Meitner et al. | 422/195 |
| 4,467,595 | 8/1984 | Kramers | 57/225 |
| 4,486,485 | 12/1984 | Sookne | 428/198 |
| 4,533,602 | 8/1985 | Nakamura et al. | 428/447 |
| 4,554,121 | 11/1985 | Kramers | 264/103 |
| 4,606,964 | 8/1986 | Wideman | 428/152 |
| 4,657,802 | 4/1987 | Morman | 428/152 |
| 4,720,415 | 1/1988 | Vander Wielen et al. | 428/152 |
| 4,725,473 | 2/1988 | Van Gompel et al. | 428/156 |

(List continued on next page.)

FOREIGN PATENT DOCUMENTS

| | | |
|---|---|---|
| 194150 A2 | 9/1986 | European Pat. Off. . |
| 309073 A2 | 3/1989 | European Pat. Off. . |
| 335614 A2 | 10/1989 | European Pat. Off. . |
| 444671 A3 | 9/1991 | European Pat. Off. . |
| 549954 A1 | 7/1993 | European Pat. Off. . |
| 554896 A1 | 8/1993 | European Pat. Off. . |
| 105629 B1 | 12/1993 | European Pat. Off. . |
| 693585 A2 | 1/1996 | European Pat. Off. . |
| 8-48804 | 2/1996 | Japan . |
| 1532467 | 11/1978 | United Kingdom . |
| 2026942 | 2/1980 | United Kingdom . |
| 2177049 | 1/1987 | United Kingdom . |
| 95/16562 | 6/1995 | WIPO . |

OTHER PUBLICATIONS

Patent Abstracts of Japan, vol. 014, No. 193 (M–0963), Apr. 19, 1990 for JP 02 036938 A (Mitsubishi Kasei Corp), Feb. 6, 1990.

Database WPI, Section Ch. Week 8918, Derwent Publications Ltd., London, GB; Class A32, AN 89–133584 XP002061495 for JP 01 077 519 A (Sekisui Chem Ind Co Ltd), Mar. 23, 1989.

Database WPI, Section Ch, Week 8514 Derwent Publications Ltd., London, GB; Class A 13, AN 85–084541 XP002061496 for JP 60 036 128 A (Denki Kagaku Kogyo K), Feb. 25, 1985.

Database WPI, Section Ch, Week 7540, Derwent Publications Ltd., London, GB; Class A18, AN 75–66512W XP002061497 for JP 50 027 072 B (Mitsubishi Rayon Plas), Sep. 4, 1975.

*Primary Examiner*—Christopher Raimund

[57] ABSTRACT

A breathable multi-layer film laminate including microporous filled film bonded to continuous film. A support layer such as a fibrous web can be adhered to the film laminate on one or both surfaces.

7 Claims, 3 Drawing Sheets

U.S. PATENT DOCUMENTS

| | | | |
|---|---|---|---|
| 4,753,834 | 6/1988 | Braun et al. | 428/74 |
| 4,761,324 | 8/1988 | Rautenberg et al. | 428/198 |
| 4,847,134 | 7/1989 | Fahrenkrug et al. | 428/138 |
| 4,863,779 | 9/1989 | Daponte | 428/152 |
| 4,892,779 | 1/1990 | Leatherman et al. | 428/220 |
| 4,902,553 | 2/1990 | Hwang et al. | 428/156 |
| 4,981,747 | 1/1991 | Morman | 428/198 |
| 5,143,679 | 9/1992 | Weber et al. | 264/288.8 |
| 5,169,706 | 12/1992 | Collier, IV et al. | 428/152 |
| 5,188,885 | 2/1993 | Timmons et al. | 428/198 |
| 5,208,098 | 5/1993 | Stover | 428/284 |
| 5,229,191 | 7/1993 | Austin | 428/198 |
| 5,266,394 | 11/1993 | Diehl et al. | 428/261 |
| 5,334,446 | 8/1994 | Quantrille et al. | 428/284 |
| 5,336,545 | 8/1994 | Morman | 428/152 |
| 5,382,400 | 1/1995 | Pike et al. | 264/168 |
| 5,393,599 | 2/1995 | Quantrille et al. | 428/284 |
| 5,409,761 | 4/1995 | Langley | 428/198 |
| 5,415,925 | 5/1995 | Austin et al. | 428/287 |
| 5,482,765 | 1/1996 | Bradley et al. | 428/286 |
| 5,484,645 | 1/1996 | Lickfield et al. | 428/198 |
| 5,536,555 | 7/1996 | Zelazoski et al. | 428/138 |
| 5,540,976 | 7/1996 | Shawver et al. | 428/198 |
| 5,543,206 | 8/1996 | Austin et al. | 428/198 |

BREATHABLE LAMINATE INCLUDING FILLED FILM AND CONTINUOUS FILM AND METHOD FOR MAKING THE SAME

This application is a division of application Ser. No. 08/774,477 entitled Breathable Laminate Including Filled Film and Continous Film and Method for Making the Same and filed in the U.S. Patent and Trademark Office on Dec. 30, 1996, now U.S. Pat. No. 5,914,184 The entirety of application Ser. No. 08/774,477 is hereby incorporated by reference.

FIELD OF INVENTION

The present invention is directed to breathable multilayer film laminates including a filled film and a continuous elongatable film. In addition, the present invention is directed to a method of making such laminates.

BACKGROUND OF THE INVENTION

The present invention is directed to breathable laminates including at least one microporous film and a continuous elongatable film and a process for making the same. Such materials have a wide variety of uses, especially in the areas of limited use and disposable items.

Films have been traditionally used to provide barrier properties in limited use or disposable items. By limited use or disposable, it is meant that the product and/or component is used only a small number of times or possibly only once before being discarded. Examples of such products include, but are not limited to, surgical and health care related products such as surgical drapes and gowns, disposable work wear such as coveralls and lab coats and personal care absorbent products such as diapers, training pants, incontinence garments, sanitary napkins, bandages, wipes packaging and the like. In personal care absorbent products such as infant diapers and adult incontinence products, films are used as the outer covers with the purpose of preventing body wastes from contaminating the clothing, bedding and other aspects of the surrounding environment of use. In the area of protective apparel including hospital gowns, films are used to prevent cross exchange of microorganisms between the wearer and the patient. In the area of packaging, films are used to allow passage of $H_2O$ and $O_2$ but not microorganisms.

Lamination of films have been used to create materials which are both impervious and somewhat cloth-like in appearance and texture. The outer covers on disposable diapers are but one example. In this regard, reference may be had to coassigned U.S. Pat. No. 4,818,600 dated Apr. 4, 1989 and U.S. Pat. No. 4,725,473 dated Feb. 16, 1988. Surgical gowns and drapes are other examples. See, in this regard, coassigned U.S. Pat. No. 4,379,102 dated Apr. 5, 1983.

A primary purpose of the film in such laminations is to provide liquid barrier properties. There is also a need for such laminates to be breathable so that they have the ability to transmit moisture vapor. Apparel made from laminations of these breathable and/or microporous films are more comfortable to wear by reducing the moisture vapor concentration and the consequent skin hydration underneath the apparel item. However, the pore size in breathable films cannot be too large, especially in protective apparel applications, such industrial or medical garments, where chemical liquid penetration presents a contamination risk to the wearer. Moreover, films containing micropores may allow passage of chemical vapors and/or viruses and thereby reduce the effectiveness of the protective apparel.

The conventional process for obtaining a breathable microporous film has been to stretch a thermoplastic film containing filler. Microvoids are created by the filler particles during the stretching process. The film is usually heated prior to these drawing processes to make the film more plastic and malleable. This drawing or stretching also orients the molecular structure within the film which increases its strength and durability in the stretched direction. The molecular orientation caused by stretching is desired to improve durability.

A film can be stretched in the machine-direction or the cross-machine direction. Stretching the film in the cross direction is particularly challenging because forces must be applied to the edges of the film to cause it to elongate. Tenter frames are commonly used. In contrast, stretching the film in the machine direction is relatively easy. It is only necessary to increase the draw, or speed ratio, between two rollers while the film is in the heated and plastic state. There is a durability problem, however, with uni-directionally-stretched films, be it machine direction or cross-direction. Uni-directional stretching causes molecular orientation in the stretched direction. This results in films that are easily torn or split along that dimension. For example, a machine-directionally oriented film has a propensity to split or tear along the machine direction. Also, the tensile characteristics of the film are dramatically increased in the machine direction, but the tensile strength in the cross-direction is significantly inferior to that of the machine direction.

These durability problems with uni-directionally stretched and oriented films are well known. Two approaches are commonly used to obviate the product durability problems resulting from these highly isotropic strength characteristics. The first is to stretch-orient the film in both the machine and cross direction. Films that have been biaxially stretched have more balanced strength properties. The second approach is to combine into a laminate one layer of machine directionally oriented film with one layer of cross-directionally oriented film. This approach is time consuming, size limiting, and costly. There is therefore a need for a uni-directionally-stretched, lightweight breathable film laminate using low-cost materials and processes that provides the laminate with both breathability, barrier and the in-use durability that are desired.

Moreover, precise control of the stretching process is usually required in order to avoid creating holes that are too large since, as previously mentioned, formation of undesirably large pores would lower the hydrohead value of the films to unacceptable low levels and thus cause leaking of liquids, odor causing molecules and microorganisms. There is therefore a need for a flexible breathable laminate and process that provides a laminate with the breathability barrier properties and the fit and comfort that are desired.

SUMMARY OF THE INVENTION

The present invention relates to a multi-layer film laminate including an oriented filled film and at least one continuous film. The filled film includes a polymeric resin and a filler that is at least 10 percent by volume of said polymeric resin. Preferably, the filled film contains from about 25 to about 50 volume percent of filler. The continuous elastic film is bonded to the filled film before stretching. The elastic film is water-vapor permeable and maybe impermeable to odor-causing molecules. Preferably, the continuous elastic film is either continuously bonded or point-bonded to the filled film. This laminate is stretched so that the filled film by itself has a water-vapor transmission value of at least 450 g/m²-24 hrs. The stretched laminate has a WVTR of at least 200 g/m²-24 hrs.

In one application, the elastic continuous film layer has an immediate recovery length that is at least about 50% of its elongation following a stretch cycling that achieved a stretched length of about 150% of the unbiased length. In another application, the elastic continuous film of the present invention may have an immediate recovery length that is at least about 50% its elongation length following a stretch cycling that achieved a stretched length of about 200% of the unbiased length. In one embodiment, the filled film layer also is elastic and has a permanent set so the micropores remain open. In another embodiment, the elastic continuous film has a permanent set that is less than the permanent set of the filled film.

The resulting oriented multi-layer film laminate is preferably flexible, breathable and liquid-repellent, and provides a barrier to unwanted molecules and microorganisms. The choice of material included in the filled film layer(s) and the continuous film(s) as well as the type of bonding used between the layers affect the stretchability, appearance and permeability of the laminate product.

In a first application, the elastic continuous film provides a support and reinforcement structure to the microporous filled film. In a second application, the continuous film remains a total barrier to liquids and a barrier to undesirable vapors, even where the laminate includes a filled film with large micropores. In a third application, the multilayer film laminate includes an elastic continuous film point-bonded to a nonelastic filled film such that the laminate product is stretchable in the orientation direction. In a fourth application, the multilayer film laminate is bonded to another support layer such as a nonwoven web.

Such multilayer film laminates as the entire article or a component have a wide variety of uses including, but not limited to, applications in packaging, protective garment articles including industrial work wear, as well as personal care absorbent articles including diapers, training pants, sanitary napkins, incontinence devices, bandages and the like. These same films also may be used in medical garments such as surgical drapes and gowns as well as various articles of clothing either as the entire article or simply as a component thereof.

DETAILED DESCRIPTION OF THE PREFERRED EMBODIMENTS

The present invention is directed to multi-layer film laminates including continuous elastic films and filled films.

The term "continuous film" as used herein describes a monolithic film that would not contain holes therein after stretching, so that the film provides a barrier and thus has a high hydrohead value.

The term "continuous bond" as used herein describes a bonding between two film surfaces wherein the bonding is essentially unbroken. In contrast, the term "point-bond" as used herein refer to a bonding between two film surfaces wherein the bonding is discontinuous and at discrete points of the surfaces.

Figure 1:
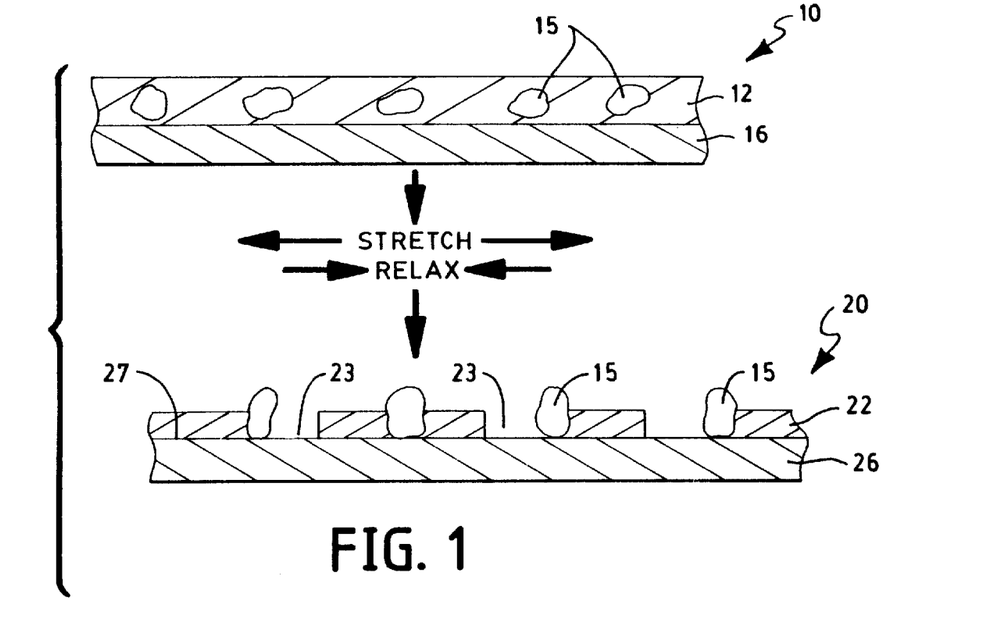
FIG. 1 is a schematic diagram of a filled film continuously bonded to a continuous film in accordance to the present invention.

Referring now to FIG. 1, an unstretched multi-layer film laminate 10 of the present invention is illustrated to contain a filled film layer 12 containing a polymeric material and fillers 15. The filled film layer 12 is continuously bonded to a continuous film layer 16 containing an elastomeric material. Upon stretching, an oriented multi-layer film laminate 20 results. Laminate 20 contains microvoids or holes 23 created by the fillers 15 during the stretching process in the oriented filled film layer 22 and an oriented continuous film layer 26.

The polymeric material of the filled film layer 12, 22 may be an elastic or nonelastic material. The term "elastic" is used herein to mean any material which, upon application of a biasing force, is stretchable, that is, elongatable (or extensible), to a stretched, biased length which is at least about 150 percent of its relaxed unbiased length, and which will recover at least 50 percent of its elongation upon release of the stretching, elongating force. A hypothetical example would be a one (1) inch sample of a material which is elongatable to at least 1.50 inches and which, upon being elongated to 1.50 inches and released, will recover to a length of not more than 1.25 inches. Many elastic materials may be stretched by much more than 50 percent of their relaxed length, for example, 100 percent or more, and many of these will recover to substantially their original relaxed length, for example, to within 105 percent of their original relaxed length, upon release of the stretching force.

As used herein, the term "nonelastic" refers to any material which does not fall within the definition of "elastic," above.

Examples of polymeric materials useful in filled film 10 include nonelastic thermoplastic polymers, elastomers, plastomers and combinations thereof.

Non-elastic thermoplastic materials useful in the present invention are extrudable thermoplastic polymers such as polyamides, nylons, polyesters, polyolefin or a blend of polyolefins including homopolymers, copolymers, and blends thereof.

Elastomers useful in the practice of this invention may be those made from copolymers such as polyurethanes, copolyether esters, polyamide polyether copolymers, ethylene vinyl acetates (EVA), block copolymers having the general formula A—B—A' or A—B like copoly(styrene/ethylene-butylene), styrene-poly(ethylene-propylene)-styrene, styrene-poly(ethylene-butylene)-styrene, (polystyrene/poly (ethylene-butylene)/polystyrene, poly(styrene/ethylene-butylene/styrene) and the like.

Useful elastomeric resins include block copolymers having the general formula A—B—A' or A—B, where A and A' are each a thermoplastic polymer endblock which contains a styrenic moiety such as a poly (vinyl arene) and where B is an elastomeric polymer midblock such as a conjugated diene or a lower alkene polymer. Block copolymers of the A—B—A' type can have different or the same thermoplastic block polymers for the A and A' blocks, and the present block copolymers are intended to embrace linear, branched and radial block copolymers. In this regard, the radial block copolymers may be designated $(A—B)_m—X$, wherein X is a polyfunctional atom or molecule and in which each $(A—B)_m—$ radiates from X in a way that A is an endblock.

In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer", and particularly "A—B—A'" and "A—B" block copolymer, is intended to embrace all block copolymers having such rubbery blocks and thermoplastic blocks. Commercial examples of such elastomeric copolymers are, for example, those known as KRATON® materials which are available from Shell Chemical Company of Houston, Tex. KRATON® block copolymers are available in several different formulations, a number of which are identified in U.S. Pat. Nos. 4,663,220, 4,323,534, 4,834,738, 5,093,422 and 5,304,599, hereby incorporated by reference.

Polymers composed of an elastomeric A—B—A—B tetrablock copolymer may also be used in the practice of this invention. Such polymers are discussed in U.S. Pat. No. 5,332,613 to Taylor et al. In such polymers, A is a thermoplastic polymer block and B is a hydrogenated isoprene. An example of such a tetrablock copolymer is a styrene-poly (ethylene-propylene)-styrene-poly(ethylene-propylene) or SEPSEP elastomeric block copolymer available from the Shell Chemical Company of Houston, Tex.

Other exemplary elastomeric materials which may be used include polyurethane elastomeric materials such as, for example, those available under the trademark ESTANE® from B. F. Goodrich & Co. or MORTHKNE® from Morton Thiokol Corp., polyester elastomeric materials such as, for example, those available under the trade designation HYTREL® from E. I. DuPont De Nemours & Company, and those known as ARNITEL®, formerly available from Akzo Plastics of Arnhem, Holland and now available from DSM of Sittard, Holland.

Another suitable material is a polyester block amide copolymer having the formula:

where n is a positive integer, PA represents a polyamide polymer segment and PE represents a polyether polymer segment. In particular, the polyether block amide copolymer has a melting point of from about 150° C. to about 170° C., as measured in accordance with ASTM D-789; a melt index of from about 6 grams per 10 minutes to about 25 grams per 10 minutes, as measured in accordance with ASTM D-1238, condition Q (235 C/1 Kg load); a modulus of elasticity in flexure of from about 20 Mpa to about 200 Mpa, as measured in accordance with ASTM D-790; a tensile strength at break of from about 29 Mpa to about 33 Mpa as measured in accordance with ASTM D-638 and an ultimate elongation at break of from about 500 percent to about 700 percent as measured by ASTM D-638. A particular embodiment of the polyether block amide copolymer has a melting point of about 152° C. as measured in accordance with ASTM D-789; a melt index of about 7 grams per 10 minutes, as measured in accordance with ASTM D-1238, condition Q (235 C/1 Kg load); a modulus of elasticity in flexure of about 29.50 Mpa, as measured in accordance with ASTM D-790; a tensile strength at break of about 29 Mpa, a measured in accordance with ASTM D-639; and an elongation at break of about 650 percent as measured in accordance with ASTM D-638. Such materials are available in various grades under the trade designation PEBAX® from ELF Atochem Inc. of Glen Rock, N.J. Examples of the use of such polymers may be found n U.S. Pat. Nos. 4,724,184, 4,820,572 and 4,923, 742 hereby incorporated by reference, to Killian et al. and assigned to the same assignee as this invention. Elastomeric polymers also include copolymers of ethylene and at least one vinyl monomer such as, for example, vinyl acetates, unsaturated aliphatic monocarboxylic acids, arid esters of such monocarboxylic acids. The elastomeric copolymers and formation of elastomeric nonwoven webs from those elastomeric copolymers are disclosed in, for example, U.S. Pat. No. 4,803,117.

The thermoplastic copolyester elastomers include copolyetheresters having the general formula:

where "G" is selected from the group consisting of poly (oxyethylene)-alpha,omega-diol, poly(oxypropylene)-alpha, omega-diol, poly(oxytetramethylene)-alpha,omega-diol and "a" and "b" are positive integers including 2, 4 and 6, "m" and "n" are positive integers including 1–20. Such materials generally have an elongation at break of from about 600 percent to 750 percent when measured in accordance with ASTM D-638 and a melt point of from about 350° F. to about 400° F. (176 to 205° C.) when measured in accordance with ASTM D-2117.

Commercial examples of such copolyester materials are, for example, those known as ARNITEL®, formerly available from Akzo Plastics of Arnhem, Holland and now available from DSM of Sittard, Holland, or those known as HYTPEL® which are available from E. I. dupont de Nemours of Wilmington, Del.

Plastomers useful in the practice of this invention have physical characters of both non-elastic thermoplastics and elastomers. Examples of useful plastomers include metallocene-catalyzed ethylene-based materials.

The term "metallocene-catalyzed ethylene-based materials" as used herein includes those polymer materials that are produced by the polymerization of at least ethylene using metallocenes or constrained geometry catalysts, a class of organometallic complexes, as catalysts. For example, a common metallocene catalyst is ferrocene, a complex with a metal sandwiched between two cyclopentadienyl (Cp) ligands. Metallocene process catalysts include bis(n-butylcyclopentadienyl)titanium dichloride, bis(n-butylcyclopentadienyl)zirconium dichloride, bis (cyclopentadienyl)scandium chloride, bis(indenyl) zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl (cyclopentadienyl,-1-flourenyl) zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow.

The metallocene process, and particularly the catalysts and catalyst support systems are the subject of a number of patents. U.S. Pat. No. 4,542,199 to Kaminsky et al. describes a procedure wherein MAO is added to toluene, the metallocene catalyst of the general formula (cyclopentadienyl)2MeRHal wherein Me is a transition metal, Hal is a halogen and P is cyclopentadienyl or a C1 to C6 alkyl radical or a halogen, is added, and ethylene is then added to form polyethylene. U.S. Pat. No. 5,189,192 to LaPointe et al. and assigned to Dow Chemical describes a process for preparing addition polymerization catalysts via metal center oxidation. U.S. Pat. No. 5,352,749 to Exxon Chemical Patents, Inc. describes a method for polymerizing monomers in fluidized beds. U.S. Pat. No. 5,349,100 describes chiral metallocene compounds and preparation thereof by creation of a chiral center by enantioselective hydride transfer.

Co-catalysts are materials such as methylaluminoxane (MAO) which is the most common, other alkylaluminums and boron containing compounds like tris(pentafluorophenyl)boron, lithium tetrakis(pentafluorophenyl)boron, and dimethylanilinium tetrakis(pentafluorophenyl)boron. Research is continuing on other co-catalyst systems or the possibility of minimizing or even eliminating the alkylaluminums because of handling and product contamination issues. The important point is that the metallocene catalyst be activated or ionized to a cationic form for reaction with the monomer(s) to be polymerized.

The metallocene-catalyzed ethylene-based polymers used in the present invention impart stretch and recovery properties to the film. Preferably, the metallocene catalyzed ethylene-based polymeris selected from copolymers of ethylene and 1-butene, copolymers of ethylene and 1-hexene, copolymers of ethylene and 1-octene and combinations thereof. In particular, preferred materials include Engage™ brand elastomeric metallocene-derived copolymers of ethylene and 1-octene, available from DuPont/Dow Elastomers of Wilmington, Del. Particularly preferred materials also include Exact™ brand metallocene-derived copolymers and terpolymers, available from Exxon Chemical Company of Houston, Tex.

In accordance with the present invention, the continuous layer 16, 26 is an elongatable material. As used herein, the term "elongatable material" as used to describe the material in the continuous layer encompasses those materials that tend to retract after being stretched at a stretch ratio of least 1.5, or 50 percent. This is believed to be the minimum stretch ratio needed to achieve a WVTR of at least 300 grams/m$^2$-24 hours. Examples of elongatable materials include elastomers and plastomers as described above. Elongatable materials further include polyolefins such as polyethylenes (especially linear low density polyethylenes), polypropylenes, and copolymers of ethylene or propylene with each other and with other alphaolefins.

In another application, where the filled film 12 is elastic, it is preferred that the polymeric material of the filled film 12 has a permanent set. The term "permanent set" as used herein, is a physical characteristic of the polymeric material such that when the material having an original length is stretched and the stretching force is removed, the sample does not return to its original length, but some length that is longer than the original length. The permanent set characteristic will allow the relaxed film 27 to retain the microvoids 23 produced from stretching.

In addition to the polymeric material, the filled film layer 10 also includes a filler which enables development of micropores during orientation of the film. As used herein a "filler" is meant to include particulates and other forms of materials which can be added to the polymer and is able to be uniformly dispersed throughout the film. The film will usually contain at least 10 percent (%), preferably about 25 to about 50 percent, filler based upon the total volume of the polymeric resin. In accordance with the present invention, the particulate size of the fillers is not critical to the product functionality. Both organic and inorganic fillers are contemplated to be within the scope of the present invention provided that they do not interfere with the film formation process.

Examples of fillers include calcium carbonate (CaCO$_3$) various kinds of clay, silica (SiO$_2$), alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, kaolin, mica, carbon, calcium oxide, magnesium oxide, aluminum hydroxide, pulp powder, wood powder, cellulose derivative, polymer particles, chitin and chitin derivatives. The filler particles may optionally be coated with a fatty acid, such as stearic acid, and behenic acid which may facilitate the free flow of the particles (in bulk) and their ease of dispersion into the polymer matrix.

The filled film 12, 22 illustrated in FIG. 1 is continuously bonded to the continuous film 16, 26. This type of bonding can be achieved by, for example, applying a continuous layer of adhesive between the layers 12, 22. Other types of continuous bonding include, for example, thermal bonding and co-extruding the layers 12, 22. Furthermore, continuous bonding may be effected by providing each film layer 12, 16 with polymeric materials having tackifiers incorporated therein.

Figure 2:
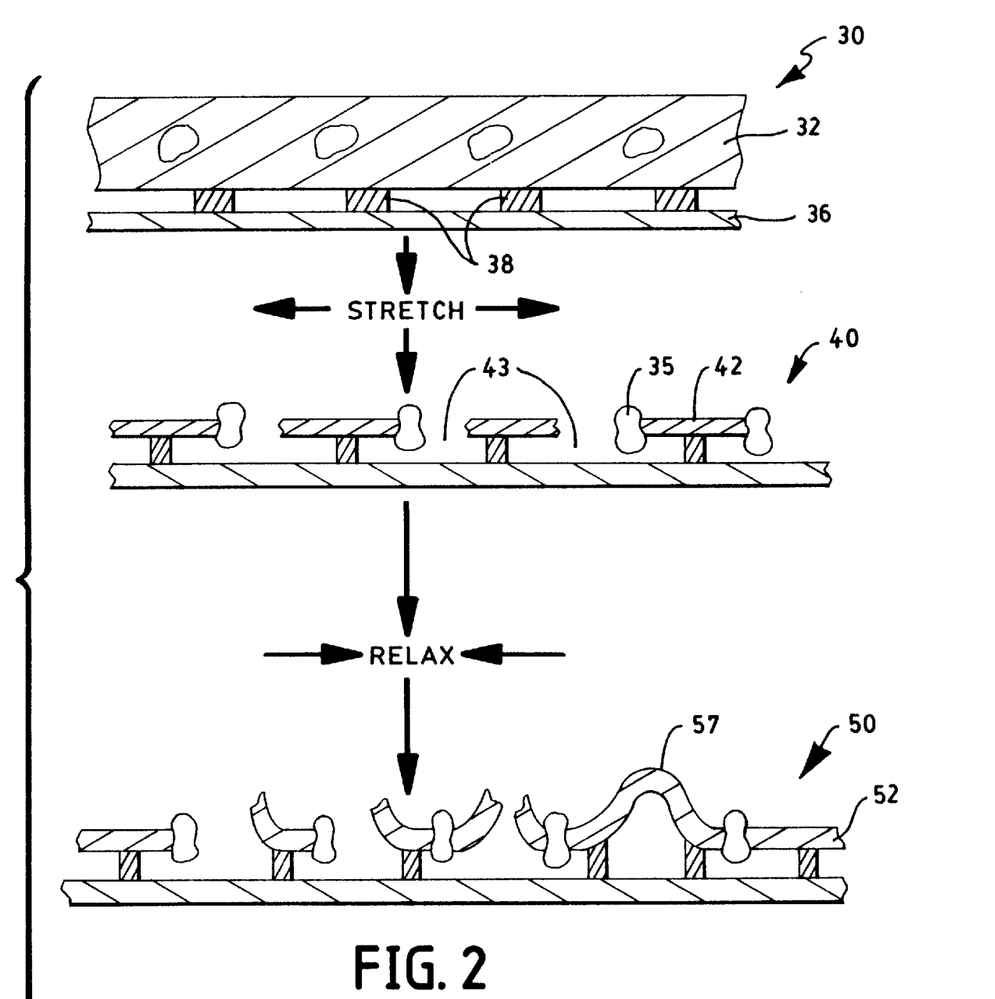
FIG. 2 is a schematic diagram of a filled film point-bonded to a continuous film in accordance to the present invention.

Alternatively, as schematically shown in FIG. 2, the film layers 32, 36 in the laminate of the present invention can be point-bonded to each other. FIG. 2 shows a laminate 30 containing a filled film 32 attached to a continuous film 36 at point-bonds 38. The laminate 30 is then stretched and results in a laminate 40 containing extended filled film layer containing microvoids 42 formed by the filler particles 34 during stretching. Once the laminate 40 is allowed to relax, the resultant laminate 50 contains a microporous filled film layer 52 with preferential retraction, i.e., with retracted resin material 57 that "pucker" upwards. The resulting retracted laminate can then be easily stretched to its original stretching length. This preferential retraction provides a more cloth-like feel to the microporous filled film 52 side of the laminate 50. In contrast, as shown in FIG. 1, the resin material 27 remain extended in a filled film layer 22 that is continuously bonded to a continuous layer 26. Bond-points 38 can be generated, for example, using adhesives, thermal point-bonding or ultrasonic bonding.

The type of bonding between the filled and continuous film and the material type of the filled film affects the characteristic of the multi-layer film laminate product. In one application, where the filled film 32 is elastic, the is polymeric resin making up the filled film 32 preferably has a permanent set characteristic that is greater than that of the continuous film layer 36 in order to obtain the "pucker" effect. In another application, where the filled film 32 is nonelastic and the cloth-like feel is preferred, point-bonding the filled film 32 to the continuous film 36 will achieve the preferential retraction in the retracted resin 57 of the laminate 50. In yet another application, where the cloth-like feel is not desired, it is preferred that the filled film 32 includes an elastomeric material having a permanent set 25 characteristic equivalent to that of the continuous film layer 36.

In addition, the type of bonding also contributes to the stretchability of the multi-layer film laminate product. As used herein, a product with a relaxed length C after it is initially oriented from an original length A to a stretched length B is "stretchable" when it could be re-stretched to length B repeatedly. Referring to FIG. 2, if the filled film 52 is nonelastic is point-bonded to an elastic continuous film 56, the resulting laminate 20 is stretchable. In contrast, referring to FIG. 1, if the filled film 22 is nonelastic is continously bonded to an elastic continuous film 26, the resulting laminate 20 is likely to not be as stretchable as the previously discussed laminate 50.

Of course, it should be understood that the present invention includes a multi-layer film laminate (not shown) wherein a plurality of layers of filled films are bonded to each other and attached to one or more layers of continuous films. In addition, the multi-layer laminate may include alternating layers of filled film and continuous film attached to each other.

Generally, it has keen possible to produce laminates with a water vapor transmission rate (WVTP) of at least about 200 grams per square meter per 24 hours, measured by the ASTM E-96-80 WVTR test with Celgard® 2500 as control. In general, factors that affect the amount of breathability include the amount of filler, the film stretching conditions (e.g., whether it is performed at ambient or elevated temperatures), orientation ratio, and film thickness. Preferably, the WVTR of the multi-film laminate of the present invention that may be used as a component in a limited-use or disposable item is between about 1,000 to about 5,000 g/m$^2$/24 hrs, depending on the application of the item.

A hydrohead value of a film or laminate is a measure of the liquid barrier properties of a material. The hydrohead test determines the height of liquid (in centimeters) which the fabric will support before a predetermined amount of liquid passes through. A fabric with a higher hydrohead reading indicates it has a greater barrier to liquid water penetration than a fabric with a lower hydrohead. The hydrohead test is performed according to Federal Test Standard 191A, Method 5514.

The permeability of the multi-film laminate will be limited by the permeability characteristic of the continuous film layer(s) in the laminate. As used herein, permeability of a film or laminate is described the permeability coefficient of the film or laminate. This coefficient has the dimensions described in Equation I below:

(I) P=[(quantity of permeant)×(film/laminate thickness)]/[(area)×(time)×(pressure drop across film/laminate)]

The type of undesirable molecule for which barriers is sought will to an extent define the composition of the continuous film layer in the laminate product. Permeability of the film layer is generally influenced by factors including its density, crystallinity, molecular mass of and crosslinking in the elongatable material as well as amount of orientation of, type of additives in the layer. Selection of the appropriate elongatable material would thereby allow selective permeability to, for example, water vapor molecules but not, for example ammonia vapor molecules (i.e. malodorous molecules) through the resulting laminate.

The desired properties can be obtained by first preparing a polymeric resin of a material as described above, filling the resin with filler, extruding a filled film made from the filled resin; secondly preparing an elastomeric resin, extruding a continuous film from the elastomeric resin, and thirdly, bonding the filled film to the continuous film. Alternatively, the unstretched filled film/continuous film may be prepared by coextrusion, a process illustrated in FIG. 3. Thereafter, stretching or orienting the filled film/continuous film laminate in at least one direction, usually, the machine direction. As explained in greater detail below, the resultant film laminate is both breathable and has barrier properties as well as increased strength properties in the orientation direction.

Figure 3:
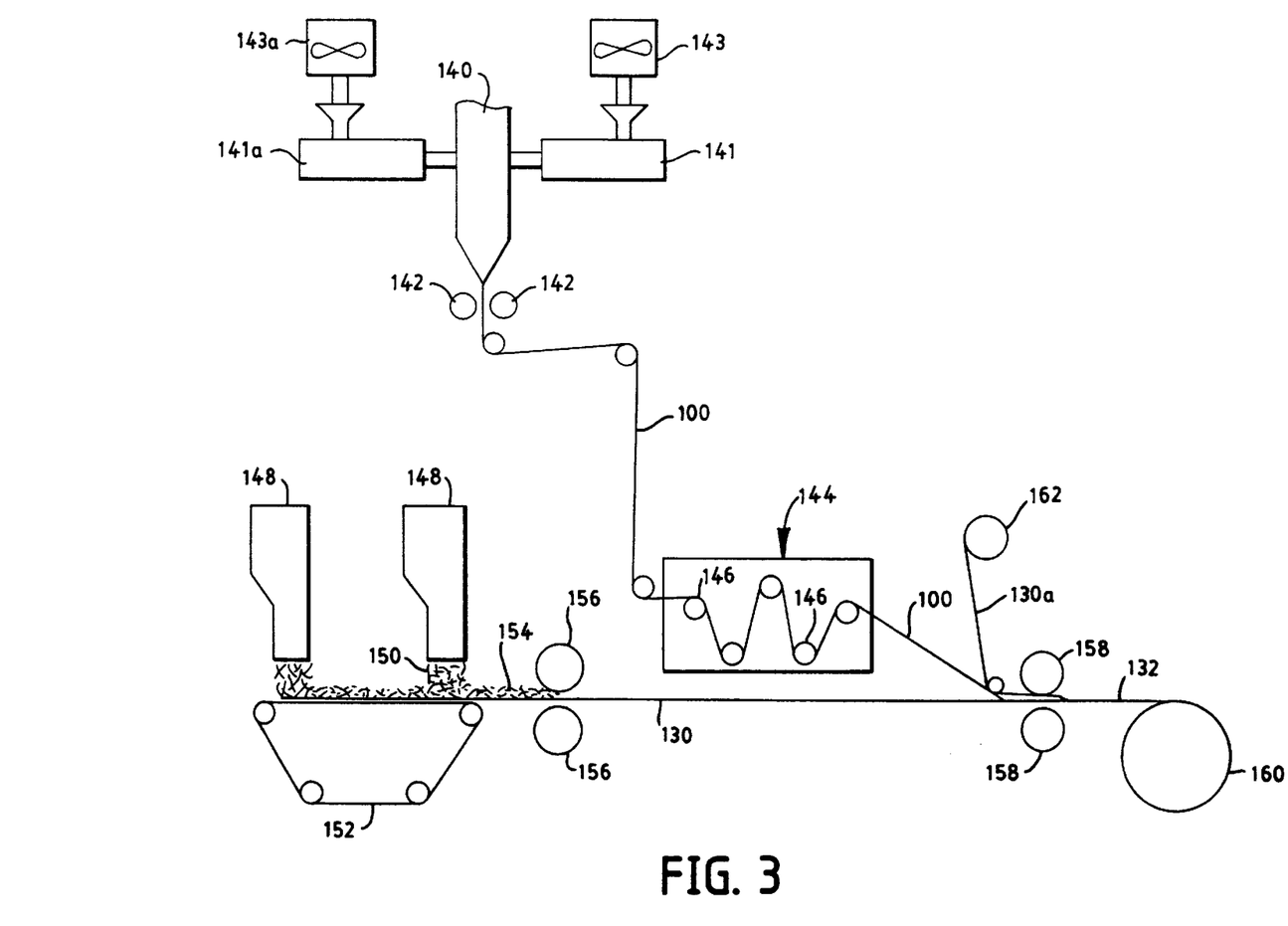
FIG. 3 is a schematic diagram of a process for preparing a multi-layer film laminate in accordance to the present invention.

In general, a process for forming filled film/continuous film laminate 100 is shown in FIG. 3 of the drawings. Referring to the figure, laminate 100 is formed from a film coextrusion apparatus 140 such as a cast or blown unit. Typically the apparatus 140 will include two extruders 141, 141a. Filled resin including the polymeric material and filler is prepared in a mixer 143 and directed to the extruder 141. Elastomeric resin is prepared in another mixer 143a and directed to extruder 141a. The laminate 100 is coextruded into a pair of nip or chill rollers 142 one of which may be patterned so as to impart an embossed pattern to the newly formed laminate 100.

From the film extrusion apparatus 140, laminate 100 is directed to a film stretching unit 144 such as a machine direction orienter, which is a commercially available device from vendors such as the Marshall and Williams Company of Providence, R.I. Such an apparatus 144 has a plurality of stretching rollers 146 moving at progressively faster speeds relative to the pair disposed before it. These rollers 146 apply an amount stress and thereby progressively stretch laminate 100 to a stretch length in the machine direction of the film which is the direction of travel of laminate 100 through the process as shown in FIG. 3. The stretch rollers 146 may be heated for better processing. Preferably, unit 144 also include rollers (not shown) upstream and/or downstream from the stretch rollers 146 that can be used to preheat the laminate 100 before orienting and/or anneal (or cool) it after stretching.

At the stretched length, a plurality of micropores form in the filled film of the laminate 100. The unfilled film remains hole free in the laminate. Preferably, the stretched length is from about 160 to about 500%, more preferably from about 200 to about 400% of the unbiased length of the film prior to stretching. If desired, laminate 100 is directed out of apparatus 144 so that the stress is removed to allow the stretched laminate 100 to relax.

It may be desirable to bond the filled film/continuous film laminate 100 to one or more substrates or support layers 130 such as is shown in FIG. 3. This further lamination of multi-layer film laminate 100 may enhance the strength and thus durability of the film laminate. If desired, film laminate 100 may be attached to one or more support layers 130 to form a reinforced laminate 132. Referring again to FIG. 3, a conventional fibrous nonwoven web forming apparatus 148, such as a pair of spunbond banks, is used to form the support layer 120. The long, essentially continuous fibers 150 are deposited onto a forming wire 152 as an unbonded web 154 and the unbonded web 154 is then sent through a pair of bonding rolls 156 to bond the fibers together and increase the tear strength of the resultant web support layer 130. One or both of the rolls are often heated to aid in bonding. Typically, one of the rolls 156 is also patterned so as to impart a discrete bond pattern with a prescribed bond surface area to the web 130. The other roll is usually a smooth anvil roll but this roll also may he patterned if so desired. Once film laminate 100 has been sufficiently stretched and the support layer 130 has been formed, the two layers are brought together and bonded to one another using a pair of laminating rolls or other means 158. As with the bonding rolls 156, the laminating rolls 158 may be heated. Also, at least one of the rolls may be patterned to create a discrete bond pattern with a prescribed bond surface area for the resultant laminate 132. Generally, the maximum bond point surface area for a given area of surface on one side of the laminate 132 will not exceed about 50 percent of the total surface area. There are a number of discrete bond patterns which may be used. See, for example, Brock et al., U.S. Pat. No. 4,041,203 which is incorporated herein by reference in its entirety. Once the laminate 132 exits the laminating rolls 158, it may be wound up into a roll 160 for subsequent processing. Alternatively, the laminate 132 may continue in-line for further processing or conversion.

While the support layers 120 and film laminate 100 shown in FIG. 3 were bonded together through thermal point bonding, other bonding means can also be used. Suitable alternatives include, for example, adhesive bonding and the use of tackifiers. In adhesive bonding, an adhesive such as a hot melt adhesive is applied between the film and the nonwoven fiber material to bind the film and nonwoven together. The adhesive can be applied by, for example, melt spraying, printing or meltblowing. Various types of adhesives are available, including those produced from amorphous polyalphaolefins, ethylene vinyl acetate-based hot melts, and Kraton® 7 brand adhesives available from Shell Chemical of Houston, Tex. and Rextac™ Brand Adhesives from Rexene of Odessa, Tex.

When the film laminate and support layer(s) are bonded with tackifiers, the tackifier may be incorporated into the film itself. The tackifier essentially serves to increase adhesion between the film and fiber layers. The multi-layer film and fiber laminate may subsequently be thermally point-bonded, although generally very little heat is required since the tackifier tends to increase the pressure sensitivity of the film and a bond somewhat like an adhesive bond can be formed. Examples of useful tackifiers include Wingtack™ 95, available from Goodyear Tire & Rubber Co. of Akron, Ohio, and Escorez™ 5300, available from Exxon Chemical Company of Houston, Tex.

If a laminate with elasticity is desired, the direction of elasticity in the laminate may be tailored by the state of the film, i.e., whether it is relaxed or stretched, during the bonding with the support layer, as well as the physical property of the support layer material. For example, if the film is still stretched while bonding to the nonwoven and the support layer is extensible in the cross-machine direction ("CD"), then a laminate with both CD and machine-direction ("MD") stretch can be produced. If the film is bonded to a non CD-extensible support layer while in a stretched state, then a laminate with a MD only stretch can be produced.

The support layers 130 and 130a as shown in FIG. 3 are fibrous nonwoven webs. The manufacture of such fibrous nonwoven webs is known. Such fibrous nonwoven webs can add additional properties to film laminate 100, such as a more soft, cloth-like feel. This is particularly advantageous when film laminate 100 is being used as a barrier layer to liquids in such applications as outer covers for personal care absorbent articles and as barrier materials for hospital, surgical, and clean room applications such as, for example, surgical drapes, gowns and other forms of apparel.

The support layer in a laminate containing the film layer of the present invention can be necked or unnecked polypropylene spunbond, crimped polypropylene spunbond, bonded carded webs, meltblown or spunbond fabrics. A particularly advantageous support layer is a fibrous nonwoven web. Such webs may be formed from a number of processes including, but not limited to, spunbonding, meltblowing and bonded carded web processes. Meltblown fibers are formed by extruding molten thermoplastic material through a plurality of fine, usually circular, capillaries as molten threads or filaments into a high velocity usually heated gas stream such as air, which attenuates the filaments of molten thermoplastic material to reduce their diameters. Thereafter, the meltblown fibers are carried by the high velocity usually heated gas stream and are deposited on a collecting surface to form a web of randomly dispersed meltblown fibers. The meltblown process is well-known and is described is various patents and publications, including NRL Report 4364, "Manufacture of Super-Fine Organic Fibers" by B. A. Wendt, E. L. Boone and D. D. Fluharty; NRL Report 5265, "An Improved Device For The Formation of Super-Fine Thermoplastic Fibers" by K. D. Lawrence, R. T. Lukas, J. A. Young; U.S. Pat. No. 3,676,242, issued Jul. 11, 1972, to Prentice; and U.S. Pat. No. 3,849,241, issued Nov. 19, 1974, to Buntin, et al. The foregoing references are incorporated herein by reference in their entirety.

Spunbond fibers are formed by extruding a molten thermoplastic material as filaments from a plurality of fine, usually circular, capillaries in a spinnerette with the diameter of the extruded filaments then being rapidly reduced, for example, by non-educative or educative fluid-drawing or other well-known spunbonding mechanisms. The production of spunbond nonwoven webs is illustrated in patents such as Appel et al., U.S. Pat. No. 4,340,563; Matsuki, et al., U.S. Pat. No. 3,802,817; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714. All of the foregoing references are incorporated herein by reference in their entirety.

A plurality of support layers 130 also may be used. Examples of such materials can include, for example, spunbond/meltblown laminates and spunbond/meltblown/spunbond laminates such as are taught in Brock et al., U.S. Pat. No. 4,041,203 which is incorporated herein by reference in its entirety.

Bonded carded webs are made from staple fibers which are usually purchased in bales. The bales are placed in a picker which separates the fibers. Next the fibers are sent through a combing or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calender rolls or ultrasonic bonding equipment is used to bond the fibers together, usually in a localized bond pattern though the web can be bonded across its entire surface if so desired. When using bicomponent staple fibers, through-air bonding equipment is, for many applications, especially advantageous.

The process shown in FIG. 3 also may be used to create a laminate wherein to support layers 130, 130a are attached to opposite surfaces of the film laminate 100. The only modification to the previously described process is to feed from a supply roll 162 of a second fibrous nonwoven web support layer 130a into the laminating rolls 158 on a side of film laminate 100 opposite that of the other fibrous nonwoven web support layer 130. One or both of the support layers may be formed directly in-line, as is support layer 130. Alternatively, the supply of one or both support layers may be in the form of a pre-formed roll 162, as is support layer 130a. In either event, the second support layer 130a is fed into the laminating rolls 158 and is laminated to film laminate 100 in the same fashion as the first support layer 130.

Figure 4:
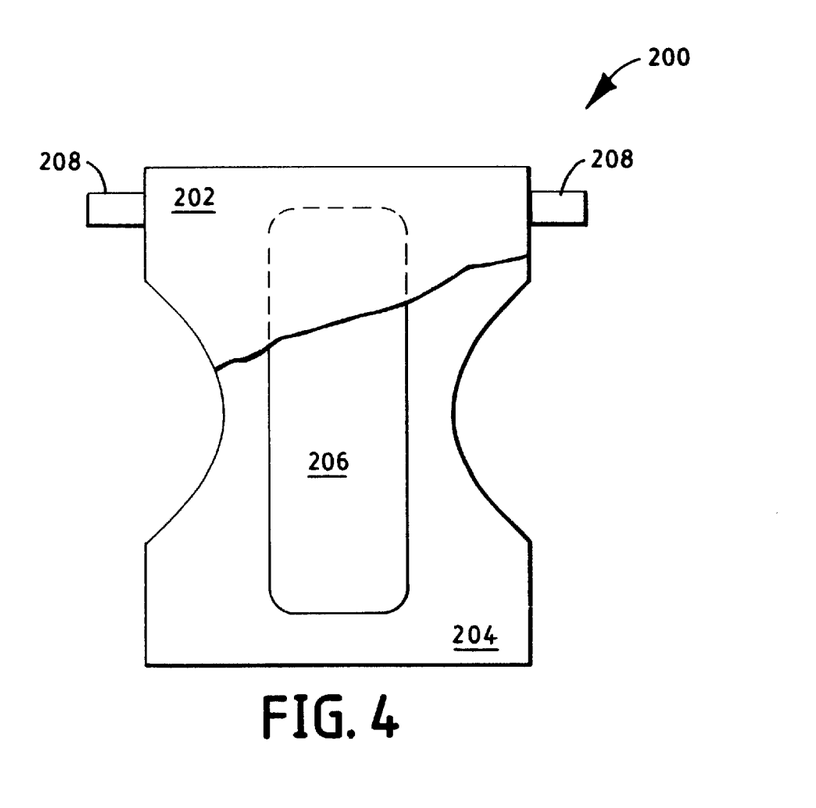
FIG. 4 is a schematic diagram of a diaper employing the multi-layer film laminate of the present invention.

As has been stated previously, breathable, barrier film laminate 100 and the breathable laminate 132 may be used in a wide variety of applications not the least of which includes personal care absorbent articles such as diapers, training pants, incontinence devices and feminine hygiene products such as sanitary napkins. An exemplary article 200, in this case a diaper, is shown in FIG. 4 of the drawings. Referring to FIG. 4, most such personal care absorbent articles 200 include a liquid permeable top sheet or liner 202, a back sheet or outercover 204 and an absorbent core 206 disposed between and contained by the top sheet 202 and back sheet 204. Articles 200 such as diapers may also include some type of fastening means 208 such as adhesive fastening tapes or mechanical hook and loop type fasteners to maintain the garment in place on the wearer. The fastening system may contain stretch material to form "stretch ears" for greater comfort.

Film laminate 100 by itself or in other forms such as the multi-film/support layer laminate 132 may be used to form various portions of the article including, but not limited to, stretch region 210, the top and the back sheet 204. If the film or laminate is to be used as the liner 202, it will most likely have to be apertured or otherwise made to be liquid permeable. When using a film/nonwoven laminate as the outercover 204, it is usually advantageous to place the nonwoven side facing out away from the user. In addition, in such embodiments it may be possible to utilize the nonwoven portion of the laminate as the loop portion of the hook and loop combination.

The advantages and other characteristics of the present invention are best illustrated by the following examples:

EXAMPLES 1–7
(Elastomeric Films and Laminates)

The following elastomeric film and laminate samples were made or obtained from suppliers. The WVTR for each film and laminate was measured using the procedure described below. The WVTR values given reflect an average of three samples for each example.

| Example | Identification Of Film Or Laminate | Basis Weight, grams/m$^2$ | Description Of Film Or Laminate | WVTR (g/m$^2$-24 hrs.) |
|---|---|---|---|---|
| 1 | Deerfield Film | 40.7 | Commercial polyurethane film (1 mil), used in Laminates A and B and the Point Bonded Laminate below. | 1270 |
| 2 | Unstretched Filled Film | 63.7 | 60% CaCO$_3$ (1 micron average particle size), 40% Engage ® CL8002 polyolefine elastomer available from DuPont/Dow Elastomers of Wilmington, D.E. | 97 |
| 3 | Stretched Filled Film | 40.8 | 60% CaCO$_3$ (1 micron average particle size), 40% Engage ® CL8002 polyolefine elastomer available from DuPont/Dow Elastomers of Wilmington, D.E. | 130 |
| 4 | Laminate A (unstretched) | 139.7 | Unstretched filled film adhesively bonded to unstretched polyurethane film (Estane 58661 from B F Goodrich, basis wt. = 40.7 gsm). | 44 |
| 5 | Laminate B (stretched) | 146.3 | Filled film adhesively bonded to polyurethane film (Estane 58661 from B F Goodrich, basis wt. = 40.7 gsm), followed by stretching of the laminate. | 89 |
| 6 | Celgard ® 2500 | 13.1 | Commercial breathable film, microporous polypropylene, available from Celanese Separation products of Charlotte, N.C. | 5000 |
| 7 | Point Bonded Laminate (stretched) | N/A | Filled film adhesively bonded at intermittent points to a polyurethane film (Estane 58661 from B F Goodrich, basis wt. = 40.7 gsm), followed by stretching of the laminate. | 110 |

Stretching of Samples

The stretched samples (e.g. Examples 3 and 5) were made by stretching in the machine direction of the films. Each sample was cut about 8 in. wide and 17 in. long. The ends were attached to wooden sticks (about 0.75 in.×0.50 in.×24 in) using Scotch tape. Each sample was wound around the sticks a couple of times for reinforcement, so that the distance between the sticks with an extended film sample in between was about 11 in. The sticks were pulled apart until the sample had been stretched by about 400% (i.e. to about 500% of its original length), and the sample was held in the elongated state for two minutes. The sample was then allowed to retract before the WVTR was measured.

Measurement of Basis Weight

Three samples from each Example were tested for basis weight. A 3-inch diameter punch die was used to cut out individual samples from each Example. The samples were weighted. The basis weights were calculated for each sample by dividing weight by area. The average basis weight for the three samples are reported above, for each Example.

Measurement of WVTR (Water Vapor Transmission Rate)

The 3-inch diameter samples from the basis weight testing were also used for testing of WVTR. Again, three samples from each Example were tested, and the results reported are average values. The WVTR was measured according to ASTM Procedure E-96-80. Each sample was placed on a WVTR testing cup to which 100cm$^3$ of tap water had been added. The WVTR cups with samples were allowed to equilibrate to room temperature and then weighed. The WVTR cups with samples were then placed in a Lindberg/Blue Model MO 1440 A forced air oven set at 38° C. and a time recorded. After the time period, the WVTR cups with samples were weighed again to determine the amount of water which had been transmitted from the cups through the samples in that time period. The results were calculated in grams of water per 24 hrs.-square meter.

Preparation of The Laminates

For Examples 4 and 5, Super 77 adhesive made by 3M Industrial Tape And Specialties Div., St. Paul Minn., was sprayed onto the filled film and the polyurethane film separately and uniformly. The two films were brought into contact with the adhesive-covered faces touching each other. The adhesive was allowed to dry for at least one hour before any handling or testing of the laminates was performed.

For Example 7, a peg board with 0.25-inch diameter holes spaced one inch apart in a square pattern was placed on top of the filled film and on top of the polyurethane film. The Super 77 adhesive was sprayed through the peg board holes onto the two films (filled film and polyurethane film) separately. The two films were removed from the peg board and attached to each other adhesive face to adhesive face. The adhesive was allowed to dry for at least one hour before any handling or testing of the laminate was performed.

Discussion of WVTR Test Results (Examples 1–7)

Stretching of the elastomeric filled films and laminates resulted in some improvement in WVTR, but the overall WVTR's were disappointing compared to the commercial Deerfield and Celgard controls. It is believed that the retraction of elastomeric films and laminates after stretching causes some of the voids formed during stretching to close. This closing of voids limits the improvements for elastomeric films and laminates.

Hydrohead Testing (Examples 1–7)

The films and laminates of Examples 1–7 were tested for hydrohead values. The liquid used for the test was a mixture of 70% isopropyl alcohol and 30% water, sold under the brand name Homebest® by Glendale Foods, Inc. of Hazelwood, Mo. The hydrohead test equipment used was the Textest Model FX3000 available from Schmid Corp. in Spartanburg, S.C.

The test procedure was as follows. The test apparatus was filled with the alcohol solution. Each sample was placed in the tester. The tester was calibrated per the manufacturer's instructions. The test was started, and liquid pressure was increased to 20 millibars. The sample were observed for liquid penetration, for at least 10 minutes under this pressure.

The results were as follows. For the Celgard film (Example 6), the liquid penetrated at less than 20 millibars pressure and formed a large puddle on the outer surface within one minute.

For the unstretched filled film (Example 2), no leaks were observed for at least six minutes. When the sample was initially exposed to the 20 millibar liquid pressure, it stretched and formed a dome about 2 in. high and 4.5 in. wide. At eight minutes, small drops were forming. At 13 minutes, the small drops covered about 15% of the exposed film surface, at a frequency of about 10 droplets/cm$^2$.

The stretched filled film (Example 3) initially resisted the liquid pressure of 20 millibars. After 4 minutes, there were numerous small droplets on the exposed surface of the film, at a frequency of about 50 droplets/cm$^2$. The film had also formed a 2-inch high dome in response to the liquid pressure. At six minutes, the small droplets were coalescing. After 8 minutes, the droplets coalesced into streams which ran down the surface of the film dome.

For the stretched laminate (Example 5), there was total resistance to the passage of liquid. At 20 millibars liquid pressure, there was no visible liquid penetration of the laminate after 10 minutes.

The polyurethane film used in the laminate was also tested by itself. At 20 millibars liquid pressure, there was no visible liquid penetration after 10 minutes, indicating that the polyurethane, contributed substantially to the resistance to penetration shown by the laminate.

EXAMPLES 8–11

Samples of the films and laminate from Examples 1, 3, 5 and 6 were prepared as described above and re-tested for WVTR in a stretched (as opposed to retracted) condition. For all of the following Examples (except Example 11), the films and laminates were initially stretched as described above, held for two minutes in the stretched condition, and allowed to retract. Unlike the above procedure, the films and laminates of Examples 8–10 were than re-stretched to about 270% of their initial length, and tested for WVTR in the re-stretched condition. The following results were achieved.

| Example | Identification Of Film Or Laminate | Corresponds To Previous Example | Basis Weight, grams/m$^2$ | WVTR In Re-Stretched condition (grams/m$^2$-24 hours) |
|---|---|---|---|---|
| 8 | Deerfield Film | 1 | 24.7 | 1530 |
| 9 | Stretched Filled Film | 3 | 28.9 | 1260 |
| 10 | Laminate B (Stretched) | 5 | 77.0 | 224 |
| 11 | Celgard ® 2500 | 6 | 14.6 | 5000 (not stretched) |

As shown above, the filled film in the re-stretched condition (Example 9) had a WVTR comparable to the Deerfield film control, and much better than the same film without re-stretching (Example 3). The laminate B had a lower WVTR, due to the presence of the adhesive and polyurethane layer. These Examples support the hypothesis that the WVTR of the stretched filled films is dependent on the amount of retraction (which tends to close the voids).

The basis weight for the samples in the stretched condition was measured by drawing a 2.25 inch diameter circle in each stretched sample. After the samples were removed from the WVTR apparatus and allowed to retract, the encircled region was cut out and weighed. In this way, the weight of each stretched sample was determined.

Therefore, the film of the present invention have high water vapor transmission rate and elasticity that impart a wide variety of functionalities including water vapor permeability, chemical-vapor and/or liquid impermeability, and comfort fit and stretch. Furthermore, such films can be attached to support layers to form laminates.

Of course, it should be understood that a wide range of changes and modifications can be made to the embodiments described above. It is therefore intended that the foregoing description illustrates rather than limits this invention, and that it is the following claims, including all equivalents, which define this invention.

I claim:

1. A process for forming a breathable, oriented filled film/continuous film laminate comprising:

providing a filled film layer including a polymeric resin and a filler in a filler amount of at least 10 percent by volume of said polymeric resin;

bonding at least one continuous film layer to said filled film layer to form a laminate, wherein said continuous film layer is elongatable, said continuous film layer is water-vapor permeable and is a barrier to malodorous molecules;

stretching said laminate to result in a stretched laminate wherein said filled film has a water vapor transmission rate of at least about 450 g/m$^2$-24 hours; and allowing said stretched laminate to relax to form a microporous film/continuous film laminate, wherein said continuous film layer remains hole-free in said stretched laminate and said stretched laminate exhibits a re-stretched water vapor transmission rate of at least about 200 g/m$^2$-24 hours.

2. The process of claim 1 wherein said filled film is bonded to said continuous film with an adhesive.

3. The process of claim 1 wherein said filled film is bonded is thermally bonded so said continuous film.

4. The process of claim 1 further comprising the step of bonding said stretched laminate to a nonwoven web.

5. The process of claim 1 further comprising the step of bonding said laminate to a nonwoven web after allowing said stretched laminate to relax.

6. The process of claim 1 wherein said continuous film and said filled film are point-bonded together.

7. The process of claim 1 wherein said continuous film and said filled film are continuously bonded together.

* * * * *